(12) United States Patent
Hari

(10) Patent No.: US 7,884,219 B2
(45) Date of Patent: Feb. 8, 2011

(54) CRYSTALLINE FORMS OF [3-(4-{2-BUTYL-1-[4-(4-CHLORO-PHENOXY)-PHENYL]-1H-IMIDAZOL-4-YL}-PHENOXY)-PROPYL]-DIETHYL-AMINE

(75) Inventor: Anitha Hari, High Point, NC (US)

(73) Assignee: TransTech Pharma, Inc., High Point, NC (US)

( * ) Notice: Subject to any disclaimer, the term of this patent is extended or adjusted under 35 U.S.C. 154(b) by 245 days.

(21) Appl. No.: 12/046,872

(22) Filed: Mar. 12, 2008

(65) Prior Publication Data

US 2008/0249316 A1    Oct. 9, 2008

Related U.S. Application Data

(60) Provisional application No. 60/921,964, filed on Apr. 5, 2007, provisional application No. 60/925,786, filed on Apr. 23, 2007.

(51) Int. Cl.
*C07D 209/44*    (2006.01)

(52) U.S. Cl. ........................................ 548/470

(58) Field of Classification Search .............. 548/335.5, 548/470
See application file for complete search history.

(56) References Cited

U.S. PATENT DOCUMENTS 7,361,678 B2 *   4/2008   Mjalli et al. ................ 514/397
2004/0082542 A1  4/2004   Mjalli et al.

FOREIGN PATENT DOCUMENTS

WO    WO 2005-000295    1/2005

OTHER PUBLICATIONS

Caira, "Crystalline Polymorphism of Organic Compounds" Topics in Current Chemistry, Springer, Berlin, DE, vol. 198, pp. 163-208, XP001156954 (1998).
International Search Report for related PCT application PCT/US2008/003325 mailed Jun. 30, 2008.
Written Opinion for related PCT application PCT/US2008/003325 mailed Jun. 30, 2008.

* cited by examiner

*Primary Examiner*—Rei-tsang Shiao

(57) ABSTRACT

The present invention relates to crystalline forms of [3-(4-{2-butyl-1-[4-(4-chloro-phenoxy)-phenyl]-1H-imidazol-4-yl}-phenoxy)-propyl]-diethylamine ("COMPOUND I") useful in the treatment of RAGE mediated diseases.

19 Claims, 10 Drawing Sheets

Figure 1. X-ray Powder Diffraction Pattern of Form I

Figure 2. X-ray Powder Diffraction Pattern of Form II

Figure 3. SSNMR spectra of Form I

Figure 4. SSNMR spectra of Form II

Figure 8. Raman spectra of Form II

CRYSTALLINE FORMS OF [3-(4-{2-BUTYL-1-[4-(4-CHLORO-PHENOXY)-PHENYL]-1H-IMIDAZOL-4-YL}-PHENOXY)-PROPYL]-DIETHYL-AMINE

CROSS REFERENCE TO RELATED APPLICATIONS

The present application claims the benefit of priority under 35 USC 119(e) from U.S. Provisional Application No. 60/921,964, filed Apr. 5, 2007, and from U.S. Provisional Application No. 60/925,786, filed Apr. 23, 2007, the disclosure of which are herein incorporated by reference in their entirety.

FIELD OF THE INVENTION

The present invention relates to crystalline forms of [3-(4-{2-butyl-1-[4-(4-chloro-phenoxy)-phenyl]-1H-imidazol-4-yl}-phenoxy)-propyl]-diethylamine ("COMPOUND I"), and its use as a therapeutic agent.

BACKGROUND OF THE INVENTION

The Receptor for Advanced Glycation Endproducts (RAGE) is a member of the immunoglobulin super family of cell surface molecules. Activation of RAGE in different tissues and organs leads to a number of pathophysiological consequences. RAGE has been implicated in a variety of conditions including: acute and chronic inflammation (Hofmann et al., *Cell* 97:889-901 (1999)), the development of diabetic late complications such as increased vascular permeability (Wautier et al., *J. Clin. Invest.* 97:238-243 (1995)), nephropathy (Teillet et al., *J. Am. Soc. Nephrol.* 11: 1488-1497 (2000)), atherosclerosis (Vlassara et. al., *The Finnish Medical Society DUODECIM, Ann. Med.* 28:419-426 (1996)), and retinopathy (Hammes et al., *Diabetologia* 42:603-607 (1999)). RAGE has also been implicated in Alzheimer's disease (Yan et al., *Nature* 382: 685-691, (1996)), erectile dysfunction, and in tumor invasion and metastasis (Taguchi et al., *Nature* 405: 354-357, (2000)).

Binding of ligands such as advanced glycation endproducts (AGEs), S100/calgranulin/EN-RAGE, β-amyloid, CML ($N^\epsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21 ras.

MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target, for down-regulation of the pathophysiological changes brought about by excessive concentrations of AGEs and other ligands for RAGE.

Thus, there is a need for the development of compounds and pharmaceutical composition that antagonize binding of physiological ligands to RAGE.

SUMMARY OF THE INVENTION

The preparation of [3-(4-{2-butyl-1-[4-(4-chloro-phenoxy)-phenyl]-1H-imidazol-4-yl}-phenoxy)-propyl]-di-ethyl-amine ("COMPOUND I") and the use thereof, such as an antagonist of the receptor for advanced glycation endproducts (RAGE) and in the treatment of various medical conditions, are described in US Patent Publication No. 2004-0082542 and in US Patent Publication No. 2005-0026811, herein incorporated by reference in their entirety. Such diseases or disease states may include, but are not limited to, acute and chronic inflammation, amyloidosis, Alzheimer's disease, cancer, tumor invasion and metastasis, kidney failure, or inflammation associated with autoimmunity, inflammatory bowel disease, rheumatoid arthritis, psoriasis, multiple sclerosis, hypoxia, stroke, heart attack, hemorrhagic shock, sepsis, organ transplantation, the development of diabetic late complications such as increased vascular permeability, diabetic nephropathy, diabetic retinopathy, a diabetic foot ulcer, a cardiovascular complication, diabetic neuropathy, impaired wound healing, erectile dysfunction, and osteoporosis. COMPOUND I and its preparation are exemplified in US Patent Publication No. 2004-0082542 in Example 406.

In one aspect, the present invention provides polymorphic forms of COMPOUND I. In one embodiment, the present invention provides a first polymorph, Form I, of COMPOUND I. In another embodiment, the present invention provides a second polymorph, Form II, of COMPOUND I. In another aspect, the present invention provides a method for producing a polymorph of COMPOUND I.

In another aspect, the present invention provides a pharmaceutical composition comprising one or more polymorphic forms of COMPOUND I.

In another aspect, the present invention provides a method of producing a pharmaceutical composition comprising one or more polymorphic forms of COMPOUND I.

In another aspect, the present invention provides a method of treating one or more RAGE mediated diseases comprising administering one or more polymorphic forms of COMPOUND I to a subject in need thereof. Embodiments of the method of treatment of the present invention may comprise administering a pharmaceutical composition comprising a therapeutically effective amount of one or more polymorphs of COMPOUND I These and other embodiments of the present invention are described in greater detail in the detailed description of the invention which follows.

DETAILED DESCRIPTION

Figure 1:
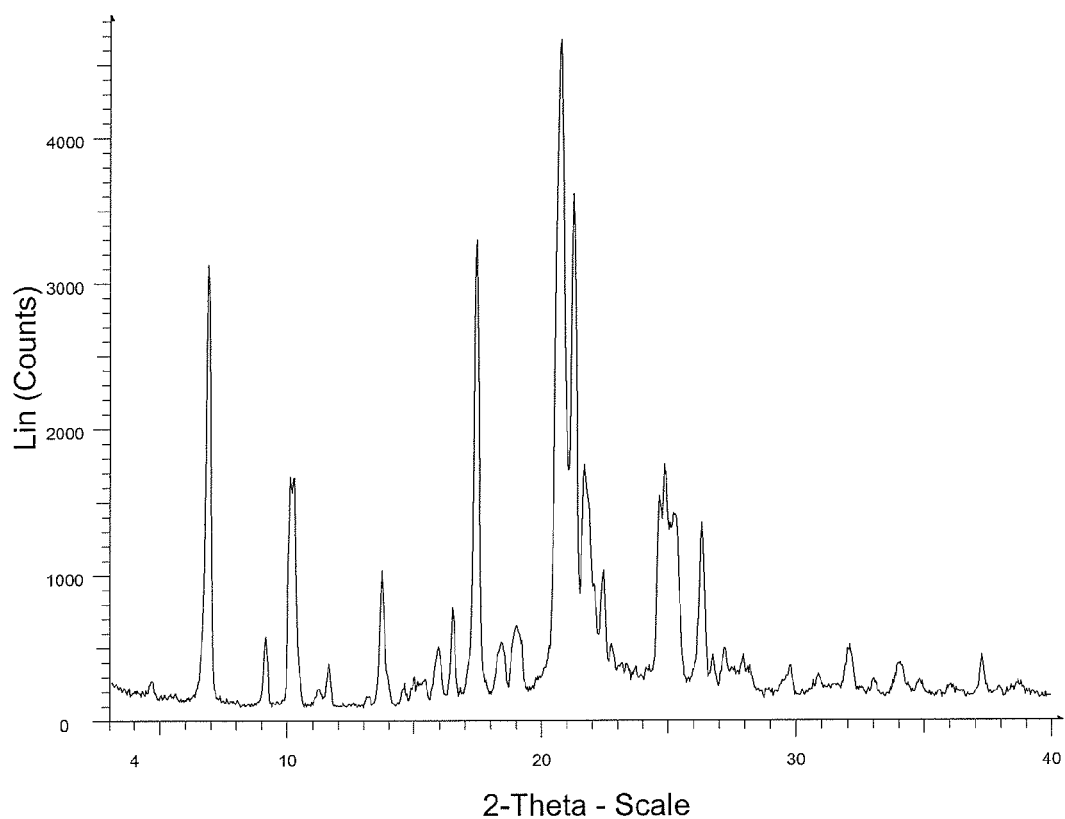
FIG. 1 is a Powder X-ray Powder Diffraction Pattern of Form I.
Figure 2:
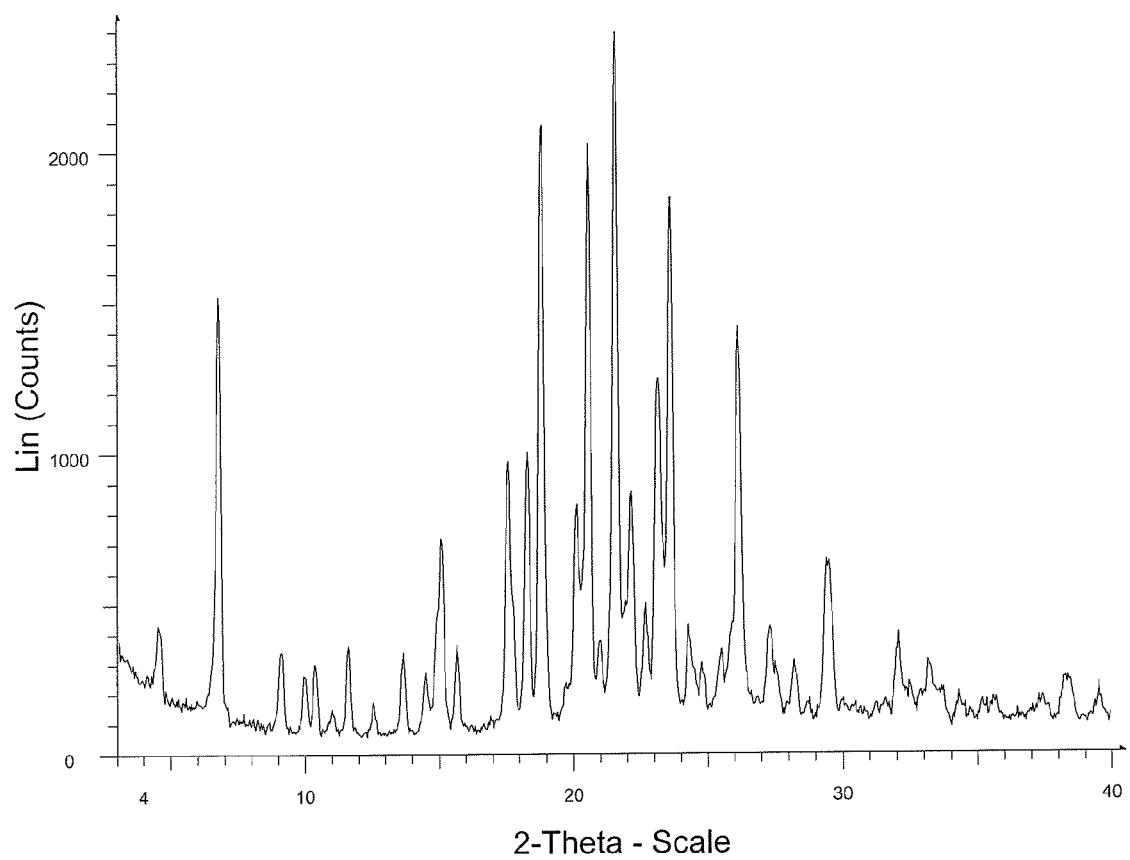
FIG. 2 is a Powder X-ray Powder Diffraction Pattern of Form II.
Figure 3:
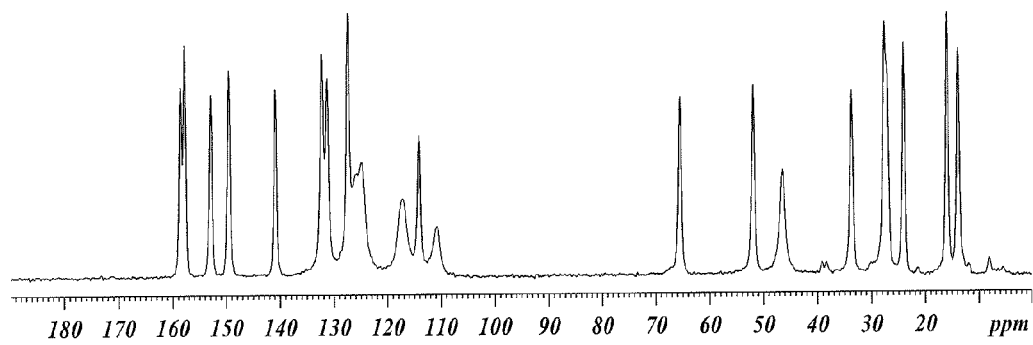
FIG. 3 is a SSNMR spectrum of Form I.
Figure 4:
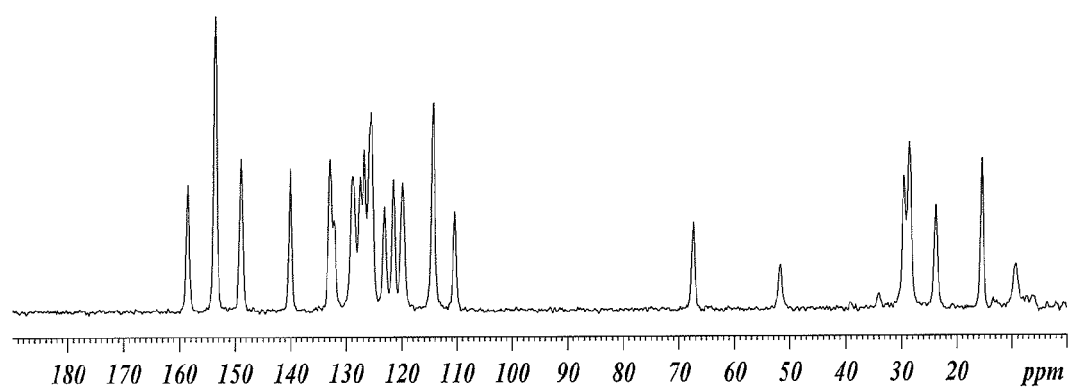
FIG. 4 is a SSNMR spectrum of Form II.
Figure 5:
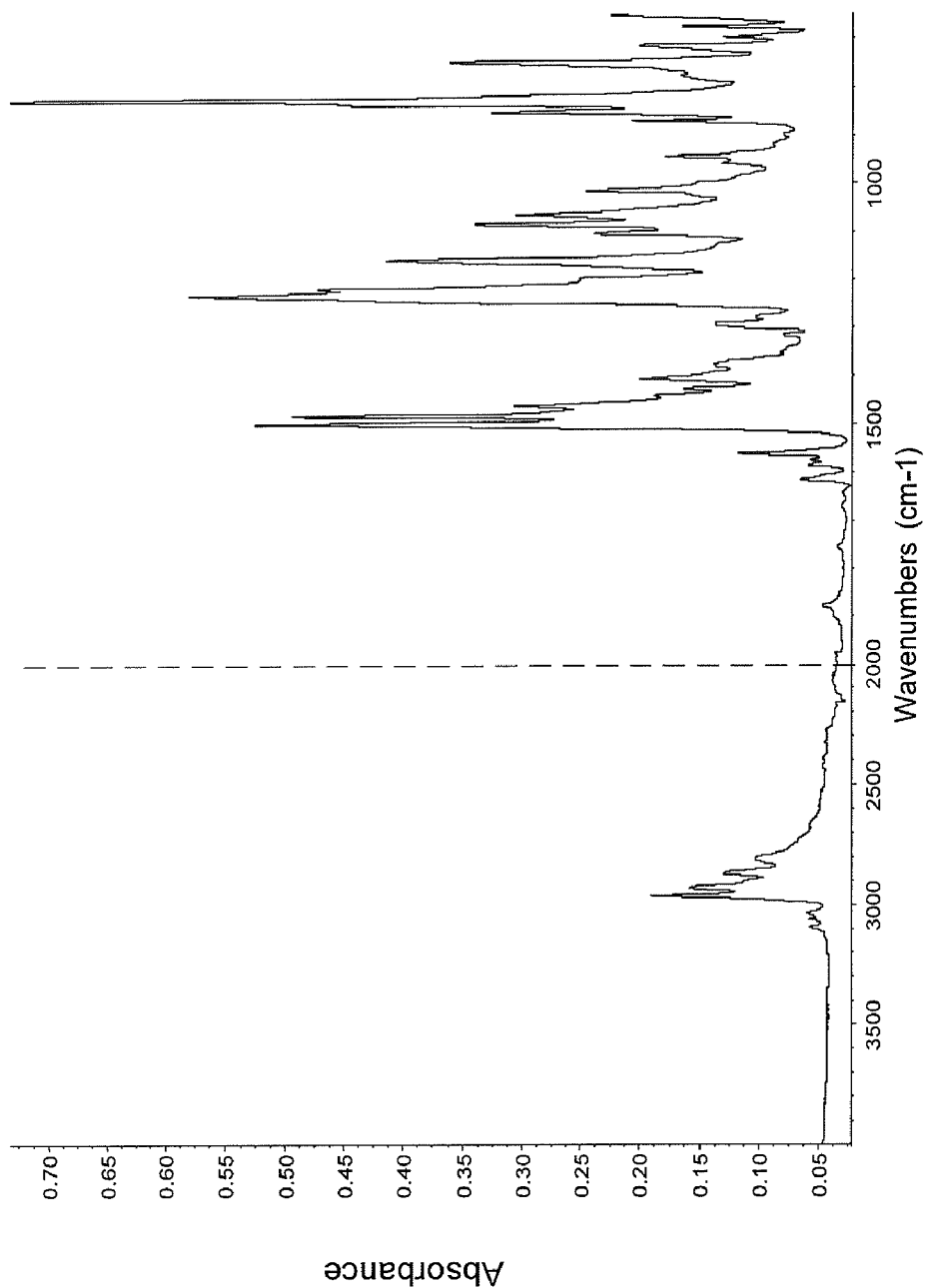
FIG. 5 is a FT-IR spectrum of Form I.
Figure 6:
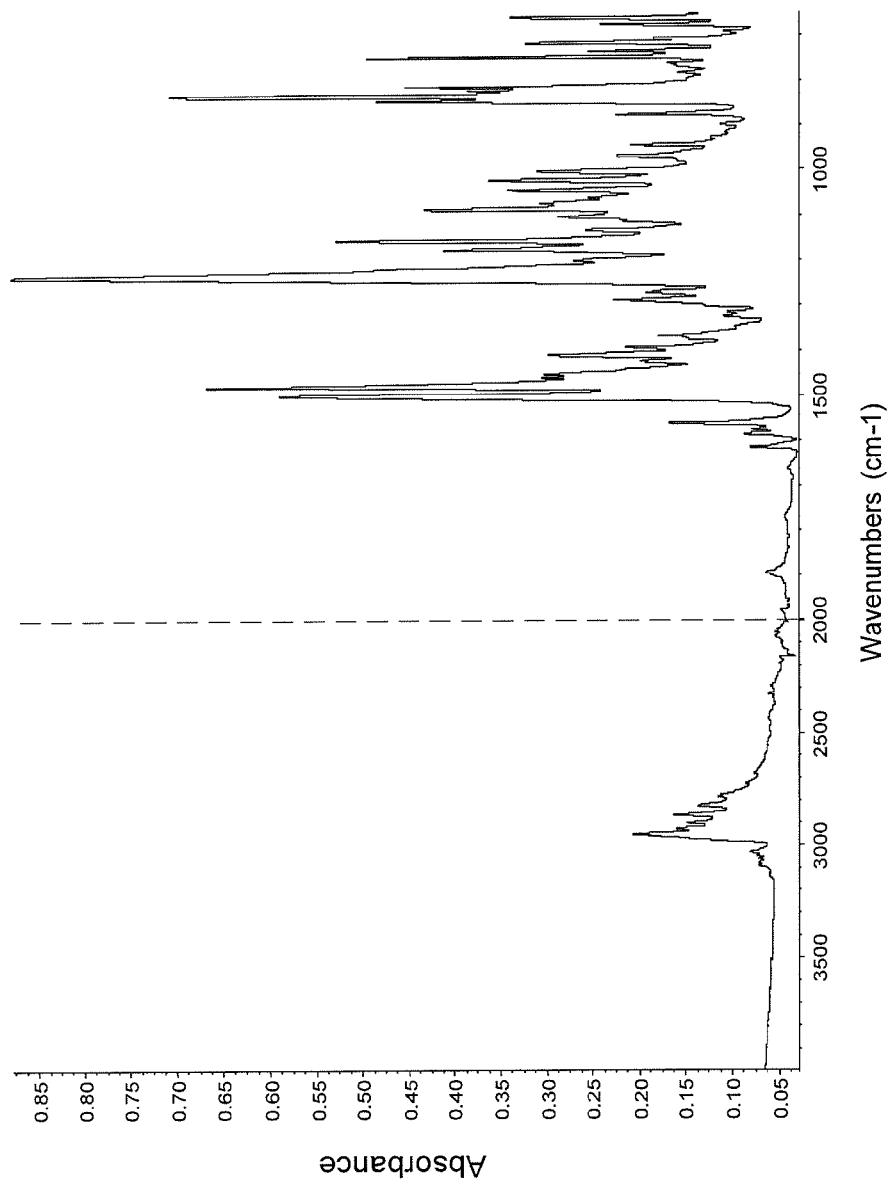
FIG. 6 is a FT-IR spectrum of Form II.
Figure 7:
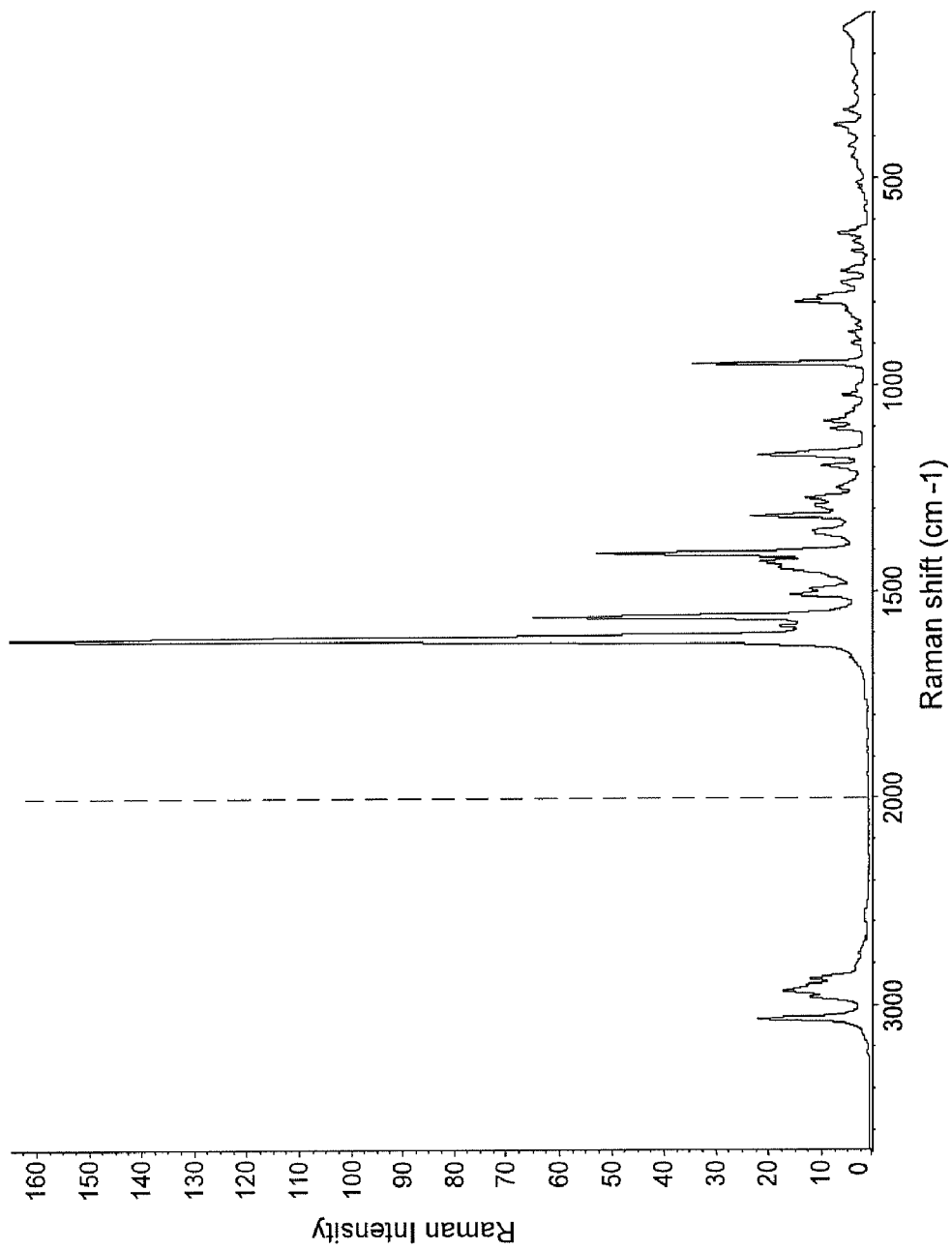
FIG. 7 is a Raman spectrum of Form I.
Figure 8:
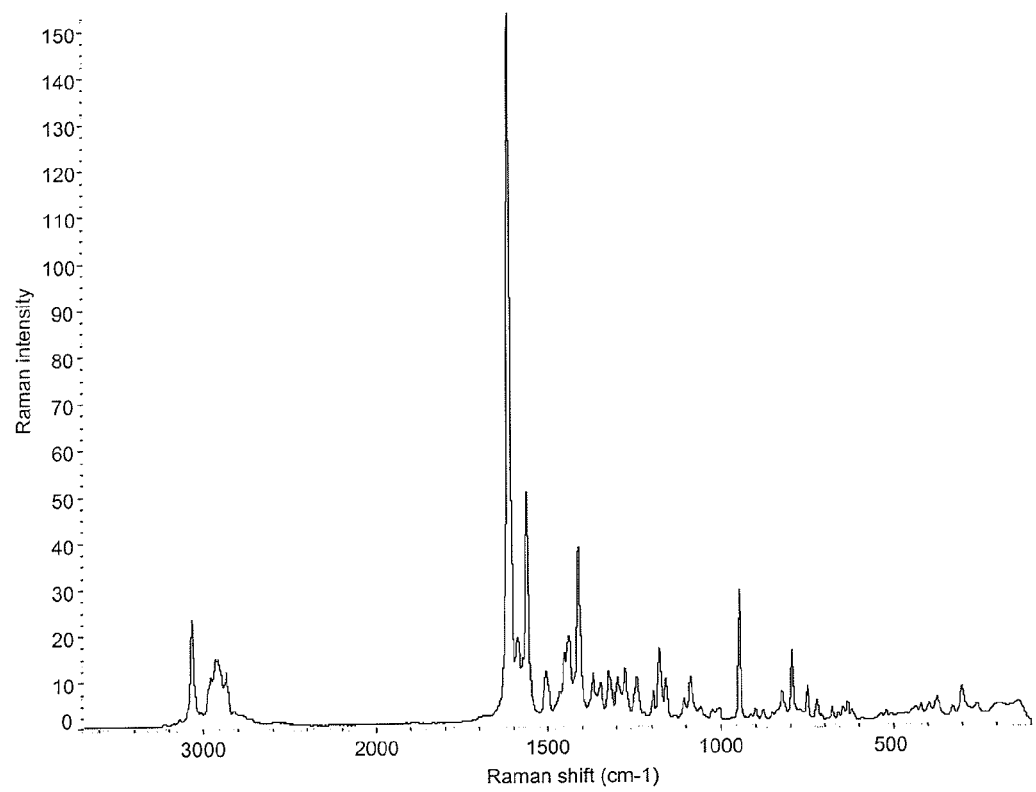
FIG. 8 is a Raman spectrum of Form II.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10. Additionally, any reference referred to as being "incorporated herein" is to be understood as being incorporated in its entirety.

By percent by weight it is meant that a particular weight of one ingredient in a composition is divided by the total weight of all of the ingredients in that composition. Percent by weight may be used interchangeably and means approximately the same as weight/weight percent or % (weight/weight) or percent by mass or mass percent. When a liquid solute is used, it is often more practical to use volume/volume percent or % (vol/vol) or percent by volume, which are all considered to be synonymous. Ppm (parts per million), ppb (parts per billion), pph (parts per hundred) are often used to indicate a percentage based on quantity and not on mass (i.e., the quantity of a given type of atom or a given type of molecule in a composition with more atoms or molecules (be it gas, liquid or solid) is divided by the total quantity of atoms or molecules in the total composition). Other terms that are used are molarity, which is the number of moles of solute per liters of solution, and molality, which is the number of moles of solution per kilograms of solution. Another concentration unit is the mole fraction, which is the moles of a given component divided by the total moles of all solution components. Mole percent is related to the mole fraction and is the mole fraction multiplied by 100.

It is further noted that, as used in this specification, the singular forms "a," "an," and "the" include plural referents unless expressly and unequivocally limited to one referent.

The term "RAGE mediated disease" is used herein to refer to one or more of the following conditions, diseases or disease states including, but are not limited to, acute or chronic inflammation including skin inflammation such as psoriasis, rheumatoid arthritis, atopic dermatitis and lung inflammation including, asthma and chronic obstructive pulmonary disease, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease including inflammation associated with autoimmunity or organ, tissue, or cell transplant, impaired wound healing, periodontal disease, neuropathy, neuronal degeneration, vascular permeability, nephropathy, atherosclerosis, retinopathy, Alzheimer's disease, erectile dysfunction, tumor invasion and/or metastasis, osteoporosis, and the development of diabetic late complications such as increased vascular permeability, nephropathy, retinopathy, and neuropathy. The pharmaceutical compositions comprising a polymorphic form of COMPOUND I also may be used to antagonize RAGE in a subject.

The term "therapeutically effective amount" is used herein to denote the amount of the polymorph of COMPOUND I that will elicit the therapeutic response of a subject that is being sought. In an embodiment, the therapeutic response may be antagonizing RAGE.

As used herein, a first polymorphic form that is "substantially free" of a second polymorphic form includes the complete absence of the second form or an amount of the second form that is not readily detectable by ordinary analytical methods. Such ordinary analytical methods include those analytical methods used to characterize Form I and Form II herein: DSC, solid state $^{13}$C NMR, Raman, X-ray powder diffraction, mid-IR (such as FT-IR) and near-IR. In an embodiment, an amount of a polymorphic form that is not readily detectable by one or more ordinary analytical methods is less than 5 percent by weight. In another embodiment, the amount of a polymorphic form that is not readily detectable by one or more ordinary analytical methods is less than 3 percent by weight. In another embodiment, the amount of a polymorphic form that is not readily detectable by one or more ordinary analytical methods is less than 2 percent by weight. In another embodiment, the amount of a polymorphic form that is not readily detectable by one or more ordinary analytical methods is less than 1 percent by weight. In another embodiment, the amount of a polymorphic form that is not readily detectable by one or more ordinary analytical methods is less than 0.5 percent by weight.

In another embodiment, the dosage or blood level of COMPOUND I and administration may be sufficient for inhibition of the biological function of RAGE at a sufficient level for sufficient time to reverse amyloidosis.

A therapeutically effective amount may be achieved in a subject by administering a dosage level of less 100 mg of compound per day. In another embodiment, the dosage level of administration is greater than 1 mg of compound per day. In another embodiment, the dosage level of administration is 5, 10 or 20 mg of compound per day.

The term "treatment" as used herein, refers to the full spectrum of treatments for a given condition or disorder from which a subject is suffering, including alleviation or amelioration of one or more of the symptoms resulting from that disorder, to the delaying of the onset or progression of the disorder.

In one aspect, the present invention provides polymorphic forms of COMPOUND I.

In one embodiment, the present invention provides Form I of COMPOUND I, having a solid state $^{13}$C NMR spectrum comprising peaks at 149.7 and 141.0 ppm.

In another embodiment, the present invention provides Form I of COMPOUND I, having a solid state $^{13}$C NMR spectrum comprising peaks at 153.0, 149.7, 141.0, 27.6, and 13.9 ppm.

In another embodiment, the present invention provides Form I of COMPOUND I, having a solid state $^{13}$C NMR spectrum comprising peaks at 157.9, 153.0, 149.7, 141.0, 131.4, 33.8, 27.6, and 13.9 ppm.

In another embodiment, the present invention provides Form I of COMPOUND I, having X-ray powder diffraction peaks expressed in degrees-2θ at 16.5 and 26.8.

In another embodiment, the present invention provides Form I of COMPOUND I, having a having X-ray powder diffraction peaks expressed in degrees-2θ at 13.1, 16.5, 22.4 and 26.8.

In another embodiment, the present invention provides Form I of COMPOUND I, having a solid state $^{13}$C NMR spectrum comprising peaks at 149.7 and 141.0 ppm and having an IR spectrum comprising peaks at 1016 and 1223 cm$^{-1}$.

In another embodiment, the present invention provides Form I of COMPOUND I, having a solid state $^{13}$C NMR spectrum comprising peaks at 149.7 and 141.0 ppm and having a Raman spectrum comprising peaks at 335 and 787 cm$^{-1}$.

In another embodiment, the present invention provides Form I of COMPOUND I, having X-ray powder diffraction peaks expressed in degrees-2θ at 16.5 and 26.8 and having an IR spectrum comprising peaks at 1016 and 1223 cm$^{-1}$.

In another embodiment, the present invention provides Form I of COMPOUND I, having X-ray powder diffraction peaks expressed in degrees-2θ at 16.5 and 26.8 and having a Raman spectrum comprising peaks at 335 and 787 cm$^{-1}$.

In another embodiment, the present invention provides Form I of COMPOUND I, having a solid state $^{13}$C NMR spectrum comprising peaks at 149.7 and 141.0 ppm and having an IR spectrum comprising peaks at 697, 870, 1016 and 1223 cm$^{-1}$.

In another embodiment, the present invention provides Form I of COMPOUND I, having a solid state $^{13}$C NMR spectrum comprising peaks at 149.7 and 141.0 ppm and having a Raman spectrum comprising peaks at 266, 293, 335, 653, 787 and 1497 cm$^{-1}$.

In another embodiment, the present invention provides Form I of COMPOUND I, having X-ray powder diffraction peaks expressed in degrees-2θ at 16.5 and 26.8 and having an IR spectrum comprising peaks at 697, 870, 1016 and 1223 cm$^{-1}$.

In another embodiment, the present invention provides Form I of COMPOUND I, having X-ray powder diffraction peaks expressed in degrees-2θ at 16.5 and 26.8 and having a Raman spectrum comprising peaks at 266, 293, 335, 653, 787 and 1497 cm$^{-1}$.

In another embodiment, the present invention provides Form I of COMPOUND I, having a Raman spectrum comprising peaks at 335 and 787 cm$^{-1}$.

In another embodiment, the present invention provides Form I of COMPOUND I, having a Raman spectrum comprising peaks at 266, 293, 335, 653, 787 and 1497 cm$^{-1}$.

In another embodiment, the present invention provides Form I of Compound I substantially free of Form II.

In another embodiment, the present invention provides a form of Compound I, which may be a crystalline form, comprising 50, 55, 60, 65, 70, 75, 80, 85, 90, 91, 92, 93, 94, 95, 96, 97, 98, or 99% or more by weight of Form I.

In another embodiment, the present invention provides Form II of COMPOUND I, having a solid state $^{13}$C NMR spectrum comprising peaks at 153.6, 140.1 and 119.9 ppm.

In another embodiment, the present invention provides Form II of COMPOUND I, having a solid state $^{13}$C NMR spectrum comprising peaks at 153.6, 149.0, 140.1, 119.9, and 28.6 ppm.

In another embodiment, the present invention provides Form II of COMPOUND I, having a solid state $^{13}$C NMR spectrum comprising peaks at 153.6, 149.0, 140.1, 123.2, 121.6, 119.9, and 28.6 ppm.

In another embodiment, the present invention provides Form II of COMPOUND I, having X-ray powder diffraction peaks expressed in degrees-2θ at 18.8 and 20.1.

In another embodiment, the present invention provides Form II of COMPOUND I, having a solid state $^{13}$C NMR spectrum comprising peaks at 153.6, 140.1 and 119.9 ppm and having an IR spectrum having peaks at 816, 1046 and 1178 cm$^{-1}$.

In another embodiment, the present invention provides Form II of COMPOUND I, having X-ray powder diffraction peaks expressed in degrees-2θ at 18.8 and 20.1 and having an IR spectrum comprising peaks at 816, 1046 and 1178 cm$^{-1}$.

In another embodiment, the present invention provides Form II of COMPOUND I, having a solid state $^{13}$C NMR spectrum comprising peaks at 153.6, 140.1 and 119.9 ppm and having a Raman spectrum having peaks at 300 and 1180 cm$^{-1}$.

In another embodiment, the present invention provides Form II of COMPOUND I, having X-ray powder diffraction peaks expressed in degrees-2θ at 18.8 and 20.1 and having a Raman spectrum comprising peaks at 300 and 1180 cm$^{-1}$.

In another embodiment, the present invention provides Form II of COMPOUND I, having a solid state $^{13}$C NMR spectrum comprising peaks at 153.6, 140.1 and 119.9 ppm and having an IR spectrum comprising peaks at 660, 707, 735, 816, 969, 1024, 1046, 1135 and 1178 cm$^{-1}$.

In another embodiment, the present invention provides Form II of COMPOUND I, having X-ray powder diffraction peaks expressed in degrees-2θ at 18.8 and 20.1 and having an IR spectrum comprising peaks at 660, 707, 735, 816, 969, 1024, 1046, 1135 and 1178 cm$^{-1}$.

In another embodiment, the present invention provides Form II of COMPOUND I, having a solid state $^{13}$C NMR spectrum comprising peaks at 153.6, 140.1 and 119.9 ppm and having a Raman spectrum comprising peaks at 257, 300, 326, 590, 646, 1180, 1348 and 1370 cm$^{-1}$.

In another embodiment, the present invention provides Form II of COMPOUND I, having X-ray powder diffraction peaks expressed in degrees-2θ at 18.8 and 20.1 and having a Raman spectrum comprising peaks at 257, 300, 326, 590, 646, 1180, 1348 and 1370 cm$^{-1}$.

In another embodiment, the present invention provides Form II of COMPOUND I, having a Raman spectrum comprising peaks at 300 and 1180 cm$^{-1}$.

In another embodiment, the present invention provides Form II of COMPOUND I, having a Raman spectrum comprising peaks at 257, 300, 326, 590, 646, 1180, 1348 and 1370 cm$^{-1}$.

In another embodiment, the present invention provides Form II of Compound I substantially free of Form I.

In another embodiment, the present invention provides a form of Compound I, which may be a crystalline form, comprising 50, 55, 60, 65, 70, 75, 80, 85, 90, 91, 92, 93, 94, 95, 96, 97, 98, or 99% or more by weight of Form II.

In another embodiment, the present invention provides a form of Compound I, which may be a crystalline form, comprising a mixture of Form I and Form II. The ratio of Form I to Form II by weight may be between 9:1 and 1:9, respectively. In an embodiment, the ratio by weight of Form I to Form II is 9:1, 8:2, 7:3, 6:4, 5:5, 4:6, 3:7, 2:8, or 1:9.

For all embodiments disclosed herein, a peak positional reproducibility is associated with the values of degree-2θ (XRPD), ppm ($^{13}$C solid state NMR), and cm$^{-1}$ (IR and Raman). Accordingly, it will be understood that all peaks disclosed herein have the value disclosed±the peak positional reproducibility associated with each analytical technique. The XRPD peak positional reproducibility is ±0.2 expressed in degree-2θ. The $^{13}$C NMR peak positional reproducibility is ±0.2 ppm. The IR peak positional reproducibility is ±2 cm$^{-1}$. The Raman peak positional reproducibility is ±2 cm$^{-1}$.

COMPOUND I and its preparation are exemplified in US Patent Publication No. 2004-0082542 in Example 406. An additional method to prepare COMPOUND I is described in the EXAMPLES section below.

In another aspect, the present invention provides a method for producing a polymorph of COMPOUND I. In an embodiment, the method of producing a polymorph of COMPOUND I comprises: heating COMPOUND I until formation of a liquid phase in a partial vacuum for a period; cooling COMPOUND I to below the temperature at which the liquid phase is formed. In an embodiment, COMPOUND I is heated to about 70° C. In another embodiment, COMPOUND I is cooled to room temperature. In another embodiment, the polymorph produced by this method is Form I. In another embodiment, COMPOUND I is precipitated from hexanes, then dissolved in ethyl acetate and followed by removal of ethyl acetate by heating above the temperature at which a liquid phase is formed.

In another embodiment, the present invention provides a method for producing a polymorph of COMPOUND I comprising: dissolving COMPOUND I in a solvent system comprising an alcoholic solvent, adding a precipitating solvent to the solvent system such that COMPOUND I precipitates from the solvent system, and recovering the precipitate from the solvent system. An alcoholic solvent is a solvent having 1 to 8 carbons and at least one —OH group and including, but not limited to, methanol, ethanol, isopropanol, n-butanol, tert-butanol, sec-butyl alcohol, furfuryl alcohol, tetrahydrofurfuryl alcohol, and polyhydric alcohols, such as ethylene glycol, and mixtures thereof. In an embodiment, the alcoholic solvent is selected from the group consisting of: methanol, ethanol, isopropanol, and mixtures thereof. In another embodiment, the precipitating solvent system comprises water. In another embodiment, the polymorph produced by this method is Form II. In another embodiment, the step of dissolving comprises heating the solvent system. The solvent system may be heated to a temperature above ambient temperature up to and including refluxing temperature.

In another embodiment, the step of recovering the precipitate from the solvent system comprises cooling the solvent system. The solvent system may be cooled to below about 0° C. In another embodiment, the method may further comprise the step of heating the collected precipitate to a temperature in a partial vacuum for a period, wherein the temperature is no greater than the temperature at which a liquid phase is formed.

To ensure no chemical transformation or degradation has occurred, the purity of each polymorph may be confirmed using HPLC and then characterized by its physio-chemical properties such as DSC, X-ray powder diffraction, infrared spectrum, Raman spectrum, and/or solid state $^{13}$C NMR.

In another aspect, the present invention provides pharmaceutical compositions comprising one or more polymorphic forms of COMPOUND I. In one embodiment, a pharmaceutical composition comprises Form I of COMPOUND I and a pharmaceutically acceptable excipient, diluent, carrier, or mixture thereof. In another embodiment, a pharmaceutical composition comprises Form II of COMPOUND I and a pharmaceutically acceptable excipient, diluent, carrier, or mixture thereof. In another embodiment, a pharmaceutical composition comprises Form I and Form II of COMPOUND I and a pharmaceutically acceptable excipient, diluent, carrier, or mixture thereof.

In another aspect, the present invention also provides methods of producing a pharmaceutical composition comprising Form I and/or Form II of COMPOUND I. In one embodiment, a method of producing a pharmaceutical composition comprises combining Form I of COMPOUND I with a pharmaceutically acceptable excipient, diluent, carrier, or a mixture thereof. In another embodiment, a method for producing a pharmaceutical composition comprises combining Form II of COMPOUND I with a pharmaceutically acceptable excipient, diluent, carrier, or a mixture thereof. In another embodiment, a method for producing a pharmaceutical composition may comprise combining Form I and Form II of COMPOUND I with a pharmaceutically acceptable excipient, diluent, carrier, or a mixture thereof.

Pharmaceutical compositions of the present invention comprising a Form I, Form II, or mixtures thereof of COMPOUND I may be in a form suitable for oral use, for example, as tablets, troches, lozenges, dispersible powders or granules, or hard or soft capsules. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations.

Tablets, tronches, lozenges, dispersible powders or granules, or hard or soft capsules may contain one or more polymorphs of COMPOUND I in admixture with non-toxic pharmaceutically-acceptable excipients which are suitable for the manufacture of such tablets, tronches, lozenges, dispersible powders or granules, or hard or soft capsules. These excipients may be for example, inert diluents, such as calcium carbonate, sodium carbonate, lactose, microcrystalline cellulose, calcium phosphate or sodium phosphate; granulating and disintegrating agents, for example corn starch, croscarmelose sodium, or alginic acid; binding agents, for example, starch, gelatin or acacia; and lubricating agents or glidants, for example magnesium stearate, stearic acid, colloidal silicon dioxide, or talc. Hard gelatin capsules may include one or more polymorphs of COMPOUND I in combination with an inert solid excipient, diluent, carrier, or mixture thereof.

A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation, the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences*, 17th ed., Mack Publishing Company, Easton, Pa. 1985, the contents of which are incorporated herein by reference.

In another embodiment, the present invention also provides pharmaceutical compositions comprising a therapeutically effective amount of COMPOUND I wherein a therapeutically effective amount of COMPOUND I comprises a sufficient amount for the treatment of a RAGE mediated disorder. In another embodiment, the present invention also provides pharmaceutical compositions comprising a therapeutically effective amount of COMPOUND I wherein a therapeutically effective amount of COMPOUND I comprises a sufficient amount for the prevention of a RAGE mediated disorder. In another embodiment, a pharmaceutical composition may comprise a therapeutically effective amount of Form I of COMPOUND I. In another embodiment, a pharmaceutical composition may comprise a therapeutically effective amount of Form II of COMPOUND I. In another embodiment, a pharmaceutical composition may comprise a therapeutically effective amount of a mixture of Form I and Form II of COMPOUND I.

In another aspect, the present invention provides a method for treating a RAGE mediated disease comprising administering one or more polymorphic forms of COMPOUND I to a subject in need thereof. The method may comprise administering a pharmaceutical composition comprising a therapeutically effective amount of COMPOUND I to a subject in need thereof.

A pharmaceutical composition of the present invention may be administered at a dosage level of less than 100 mg of compound per day. In another embodiment, the dosage level of administration is greater than 1 mg of compound per day. The amount of active ingredient that may be combined with the carrier materials to produce a single dosage will vary depending upon the host treated and the particular mode of administration. For example, in one non-limiting embodiment, a dosage unit forms, such as a tablet or capsule, intended for oral administration to humans may contain less than 100 mg of COMPOUND I with an appropriate and convenient amount of carrier material. In another embodiment, the dosage level of administration is greater than 1 mg of compound per day. In another embodiment, the dosage level of administration is 5, 10 or 20 mg of compound per day.

The dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination and the severity of the particular disease undergoing therapy.

EXAMPLES

Analytical Methods

X-Ray Powder Diffraction Analysis

The X-ray powder diffraction patterns of Form I and Form II were carried out on a Bruker D5000 diffractometer using copper radiation (wavelength: 1.54056 Å). The tube voltage and amperage were set to 40 kV and 40 mA, respectively. The divergence and scattering slits were set at 1 mm, and the receiving slit was set at 0.6 mm. Diffracted radiation was detected by a Kevex PSI detector. A theta-two theta continuous scan at 2.4°/min (1 sec/0.04° step) from 3.0 to 40° 2θ was used. An alumina standard was analyzed to check the instrument alignment. Data were collected and analyzed using Bruker axis software Version 7.0. Samples were prepared by placing them in a quartz holder. Eva Application 7.0.0.1 software was used to visualize and evaluate XRPD spectra. XRPD data files (.raw) were not processed prior to peak searching. Generally, a Threshold value of 1 and a Width value of 0.3 were used to make preliminary peak assignments. The output of automated assignments was visually checked to ensure validity and adjustments manually made if necessary.

The XRPD peak positional reproducibility is ±0.2 expressed in degree-2θ.

Solid-State Nuclear Resonance Spectroscopy $^{13}$C SSNMR Method: Approximately 80 mg of sample was tightly packed into a 4 mm ZrO spinner. The spectra were collected at low temperature (nominally at 270 K; to compensate for frictional heating due to spinning) and pressure on a Bruker-Biospin 4 mm BL triple resonance CPMAS probe positioned into a wide-bore Bruker-Biospin Avance DSX 500 MHz NMR spectrometer. The sample was positioned at the magic angle and spun at 15.0 kHz to minimize the intensities of the spinning side bands. The number of scans was adjusted to obtain adequate signal to noise ratio.

The $^{13}$C solid state spectrum was collected using a proton decoupled cross-polarization magic angle spinning experiment (CPMAS). A proton decoupling field of approximately 90 kHz was applied. The cross-polarization contact time of 2 ms was used. A minimum of 330 scans were collected for each sample. The recycle delay was adjusted to approximately 1.5 $T_{1H}$. The spectrum was referenced using an external standard of crystalline adamantane, setting its upfield resonance to 29.5 ppm.

The $^{13}$C NMR peak positional reproducibility is ±0.2 ppm.

IR Spectroscopy

Instrument Method: The IR spectra were acquired using a ThermoNicolet Magna 560 FT-IR spectrometer equipped with a KBr beamsplitter and a d-TGS KBr detector. A Specac Golden Gate Mk II single reflection diamond ATR accessory was used for sampling. The spectra were collected at 4 cm$^{-1}$ resolution with 100 co-added scans. The collection range was 4000-650 cm$^{-1}$. Happ-Genzel apodization was used. No additional sample preparation is needed with the ATR technique. Peaks were identified using the ThermoNicolet Omnic 6.0a software peak picking algorithm. Generally, a Threshold value of 0 and a Sensitivity value of 90 were used to make preliminary peak assignments. The output of automated assignment was visually checked to ensure validity. Manual adjustments were made if deemed necessary. Additional peaks between 3200-2600 cm$^{-1}$, 2400-1800 cm$^{-1}$ and 1800-650 cm$^{-1}$ were assigned at a Sensitivity of 100 if appropriate. These settings were chosen such that unresolved shoulders were not identified as separate peaks.

The IR peak positional reproducibility is ±2 cm$^{-1}$.

Raman Spectroscopy

Instrument Method: The Raman spectra were collected using a ThermoNicolet 960 FT-Raman spectrometer equipped with a 1064 nm NdYAG laser and InGaAs detector. Samples were analyzed in NMR tubes. The spectra were collected using 1 W of laser power and 100 co-added scans. The collection range was 3700-100 cm$^{-1}$. Peaks were identified using the ThermoNicolet Omnic 6.0a software peak picking algorithm. Generally, a Threshold value of 0 and a Sensitivity value of 90 were used to make preliminary peak assignments. The output of automated assignment was visually checked to ensure validity. Manual adjustments were made if deemed necessary. Additional peaks between 3300-2500 cm$^{-1}$ and 1700-100 cm$^{-1}$ were assigned at a Sensitivity of 100 if appropriate. These settings were chosen such that unresolved shoulders were not identified as separate peaks. All spectra were recorded using 4 cm$^{-1}$ resolution and Happ-Genzel apodization. Wavelength calibration was performed using polystyrene.

The Raman peak positional reproducibility is ±2 cm$^{-1}$.

Thermogravimetry Analysis (TGA)

TGA was carried out on a TA Instruments 2950 thermogravimetric analyzer. The calibration standards were nickel and Alumel™. The sample was placed in an aluminum sample pan and inserted in the TG furnace. The sample was first equilibrated at 25° C., and then heated under a stream of nitrogen at a heating rate of 10° C./min up to a final temperature of 350° C.

Differential Scanning Calorimetry

DSC Method A: DSC may be performed using a TA Instruments 2920 differential scanning calorimeter. The sample is placed into an aluminum DSC pan and the weight is accurately recorded. The pan is covered with a lid and then crimped. The sample cell is equilibrated at 25° C. and heated under a nitrogen purge at a rate of 10° C./min, up to a final temperature of 250° C. Indium metal is used as the calibration standard. Reported temperatures are at the transition maxima.

DSC Method B: DSC may also be performed on a Mettler AT 261 differential scanning calorimeter. For DSC Method B, the sample is placed into an aluminum DSC pan and the weight is accurately recorded. The pan is covered with a lid and then crimped. The sample is equilibrated at 25° C. and heated under a nitrogen purge at a rate of 10° C./min up to a final temperature of 150° C. Reported temperatures are at the transition maxima.

Preparation of Compound I

To a solution of 4-acetoxyacetophenone (1.0 eq) in dichloromethane on an ice bath was added bromine (1.05 eq). The bromine was added slowly at 0° C. The ice bath was removed and stirring continued at the ambient temperature until the reaction was complete (monitored by HPLC). The reaction mixture was concentrated in vacuum to provide 4-acetoxy-α-bromoacetophenone that was used without further purification.

To a solution of 4-acetoxy-α-bromoacetophenone (1.0 eq) and sodium bicarbonate (1.9 eq) in methanol/dichloromethane (8/1) at room temperature was added 4-chlorophenoxyaniline (1.0 eq). After the reaction was complete (as indicated by HPLC), the mixture was filtered, and the resulting aminoacetophenone derivative (yellow solid) was washed with methanol, and dried in vacuum. The aminoacetophenone derivative then was washed with water followed by methanol and dried under vacuum at 30-60° C.

To a solution of the aminoacetophenone derivative (1.0 eq), triethylamine (2.0 eq) in dichloromethane on an ice bath was added valeryl chloride (1.5 eq). The reaction was monitored by HPLC. After the reaction was complete, the mixture was allowed to warm to room temperature, and the solvents were removed under vacuum. Ethylacetate was added to dissolve the N-(4-chlorophenoxyphenyl)-N-(4-acetoxybenzoylmethyl)-n-pentanamide product, and the solution was filtered. Ethylacetate was removed in vacuum to obtain the product as a yellow liquid which was used without further purification.

A solution of the N-(4-chlorophenoxyphenyl)-N-(4-acetoxybenzoylmethyl)-n-pentanamide (1.0 eq) in acetic acid and ammonium acetate was heated at 100-110° C. After the reaction was complete (indicated by HPLC), the mixture was cooled and added to chilled water. The resulting solid was filtered, washed with water, air dried, then washed with diethylether followed by ethylacetate, air dried and finally dried in vacuum at 30-60° C. to give 4-{1-[4-(4-chlorophenoxy)phenyl]-2-(1-butyl)-1H-imidazol-4-yl}phenol.

In the final step, COMPOUND I was synthesized by the alkylation of 4-(1-[4-(4-chlorophenoxy)phenyl]-2-(1-butyl)-1H-imidazol-4-yl)phenol with 3-diethylamino-1-chloro-propane in the presence of potassium carbonate.

The 3-diethylamino-1-chloropropane was synthesized by the reaction of 3-diethylamino-1-propanol (1.0 eq) with thionyl chloride (2.0 eq) in chloroform. The product was extracted in diethyl ether, and the solvent was removed under vacuum and purified by distillation.

The 4-(1-[4-(4-chlorophenoxy)phenyl]-2-(1-butyl)-1H-imidazol-4-yl)phenol (1.0 eq) and the 3-diethylamino-1-chloropropane (1.05 eq) were refluxed in acetone in the presence of potassium carbonate (1.5 eq). After the reaction was complete (indicated by HPLC), the mixture was cooled to room temperature and filtered. The filtered solution was concentrated under vacuum, and COMPOUND I may be precipitated with hexane, filtered, and dried in vacuum. The product may be further purified by dissolving in ethyl acetate, washing with sodium carbonate solution followed by sodium chloride solution. The organic layer may then be dried with magnesium sulfate. The ethyl acetate may then be removed under vacuum and COMPOUND I dried under vacuum at a temperature above or below the temperature at which a liquid phase is formed.

The filtered solution may also be precipitated from acetone/hexane. The collected precipitate may then be dissolved in methanol and precipitated by the addition of water, followed by filtration and drying under vacuum at a temperature below the temperature at which a liquid phase is formed.

Form I

Form I of COMPOUND I can be prepared according to the following method.

A 3 kg lot of COMPOUND I was prepared via the synthesis described in Example B, where the final step involves precipitation of COMPOUND I from hexanes, then dissolving in ethyl acetate and subsequent removal of residual ethyl acetate in vacuo at 70° C. At this temperature a liquid phase is formed. The liquid COMPOUND I was poured into trays for drying and removal of solvent. Upon cooling to room temperature, the solid COMPOUND I was broken into pieces and milled using a mortar and pestle to provide Form I.

Form I was characterized by X-ray powder diffraction (XRPD), infrared spectroscopy, solid state $^{13}$C NMR, Raman spectroscopy, differential scanning calorimetry (DSC), and thermogravimetric analysis.

Crystalline Form I is characterized by the following X-ray powder diffraction pattern expressed in terms of the degree 2θ and relative intensities with a relative intensity of ≧3.4% measured on a Bruker D5000 diffractometer with CuKα radiation:

| X-ray Powder Diffraction Peaks for Crystalline Form I | |
|---|---|
| Angle (Degree 2θ) | Relative Intensity* % |
| 4.6 | 5.7 |
| 5.5 | 3.9 |
| 6.8 | 67.0 |
| 9.1 | 12.3 |
| 10.2 | 35.4 |
| 11.2 | 4.5 |
| 11.6 | 8.3 |
| 13.1 | 3.4 |
| 13.7 | 21.9 |
| 14.6 | 5.3 |
| 15.0 | 6.3 |
| 15.4 | 5.9 |
| 15.9 | 10.8 |
| 16.5 | 16.5 |
| 17.4 | 70.6 |
| 18.4 | 11.5 |
| 19.0 | 13.9 |
| 20.7 | 100.0 |
| 21.3 | 77.3 |
| 21.7 | 37.4 |
| 22.4 | 22.0 |
| 22.8 | 11.2 |
| 23.1 | 8.2 |
| 23.4 | 8.2 |
| 23.7 | 7.8 |
| 24.2 | 8.0 |
| 24.7 | 32.8 |
| 24.9 | 37.5 |
| 25.3 | 30.1 |
| 26.3 | 28.9 |
| 26.8 | 9.5 |
| 27.2 | 10.6 |
| 28.0 | 9.5 |
| 29.8 | 7.9 |
| 30.9 | 6.8 |
| 32.1 | 11.0 |
| 33.0 | 6.0 |

-continued

X-ray Powder Diffraction Peaks for Crystalline Form I

| Angle (Degree 2θ) | Relative Intensity* % |
|---|---|
| 34.1 | 8.4 |
| 34.8 | 5.9 |
| 37.3 | 9.5 |
| 38.0 | 4.9 |
| 38.7 | 5.8 |

*The relative intensities may change depending on the crystal size and morphology.

Representative values of degree 2θ for Form I are 13.1, 16.5, 22.4 and 26.8. Particularly representative values of degree 2θ for Form I are 16.5 and 26.8.

Crystalline Form I is characterized by the following $^{13}$C Solid State NMR shifts.

$^{13}$C chemical shifts of Form I

| $^{13}$C Chemical Shifts$^a$ [ppm] | Intensity$^b$ |
|---|---|
| 158.7 | 8.6 |
| 157.9 | 10.6 |
| 153.0 | 8.2 |
| 149.7 | 9.4 |
| 141.0 | 8.5 |
| 132.4 | 10.1 |
| 131.4 | 8.9 |
| 127.6 | 12.0 |
| 125.9 | 4.5 |
| 125.0 | 5.0 |
| 117.4 | 3.3 |
| 114.2 | 6.3 |
| 110.8 | 2.0 |
| 65.6 | 8.0 |
| 52.0 | 8.5 |
| 46.6 | 4.6 |
| 33.8 | 8.3 |
| 27.6 | 11.4 |
| 27.2 shoulder | — |
| 24.1 | 10.4 |
| 16 | 11.9 |
| 13.9 | 10.2 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Representative $^{13}$C NMR chemical shifts for Form I are as follows:

| Form I $^{13}$C Chemical Shifts [ppm] |
|---|
| 157.9 |
| 153.0 |
| 149.7 |
| 141.0 |
| 131.4 |
| 33.8 |
| 27.6 |
| 13.9 |

Form I is characterized by the following FT-IR peaks:

| FT-IR Peak List of Form I Wavelength (cm$^{-1}$) |
|---|
| 652 |
| 675 |
| 697 |
| 715 |
| 749 |
| 777 |
| 829 |
| 853 |
| 870 |
| 898 |
| 919 |
| 945 |
| 958 |
| 1016 |
| 1067 |
| 1086 |
| 1105 |
| 1162 |
| 1200 |
| 1223 |
| 1236 |
| 1279 |
| 1294 |
| 1318 |
| 1353 |
| 1379 |
| 1408 |
| 1429 |
| 1444 |
| 1465 |
| 1486 |
| 1503 |
| 1563 |
| 1576 |
| 1588 |
| 1617 |
| 1882 |
| 1899 |
| 1981 |
| 2051 |
| 2163 |
| 2276 |
| 2324 |
| 2391 |
| 2672 |
| 2731 |
| 2803 |
| 2813 |
| 2869 |
| 2900 |
| 2927 |
| 2961 |
| 3033 |
| 3061 |
| 3093 |
| 3133 |

Representative FT-IR peaks for Form I are as follows:

| Form I Wavenumber (cm$^{-1}$) |
|---|
| 697 |
| 870 |
| 1016 |
| 1223 |

Form I is characterized by the following Raman peaks:

| Representative Raman Peaks of Form I |
| --- |
| 139 |
| 192 |
| 198 |
| 208 |
| 217 |
| 266 |
| 293 |
| 335 |
| 371 |
| 389 |
| 422 |
| 448 |
| 475 |
| 511 |
| 525 |
| 571 |
| 620 |
| 633 |
| 653 |
| 677 |
| 698 |
| 724 |
| 753 |
| 787 |
| 798 |
| 821 |
| 834 |
| 855 |
| 871 |
| 880 |
| 898 |
| 947 |
| 1004 |
| 1010 |
| 1024 |
| 1055 |
| 1075 |
| 1088 |
| 1106 |
| 1170 |
| 1197 |
| 1250 |
| 1274 |
| 1293 |
| 1318 |
| 1354 |
| 1362 |
| 1410 |
| 1430 |
| 1444 |
| 1497 |
| 1510 |
| 1563 |
| 1586 |
| 1618 |
| 2571 |
| 2871 |
| 2902 |
| 2932 |
| 2962 |
| 3063 |

Particularly representative Raman peaks for Form I are as follows:

| Form I Wavenumber (cm$^{-1}$) |
| --- |
| 266 |
| 293 |
| 335 |
| 653 |
| 787 |
| 1497 |

Figure 9:
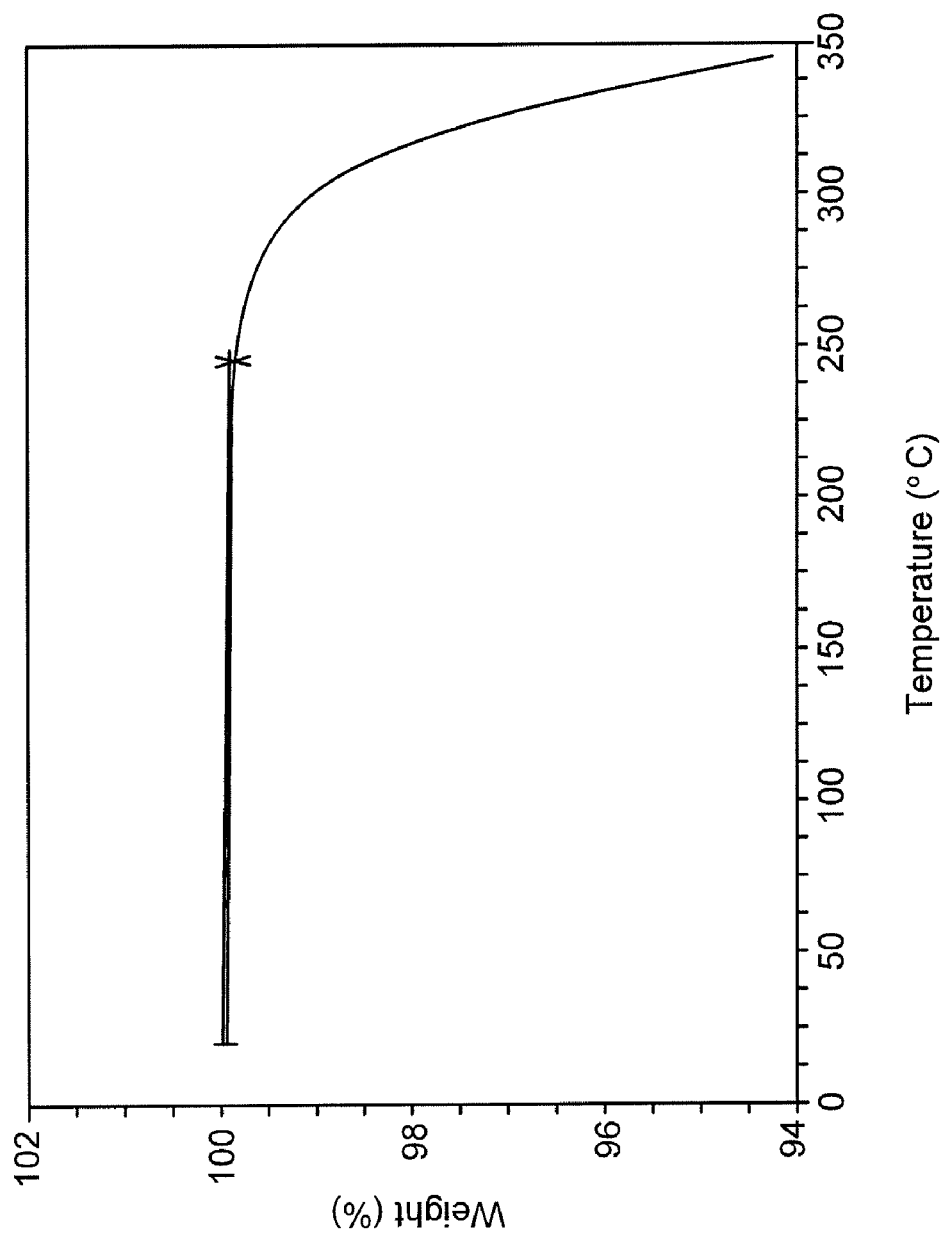
FIG. 9 is a thermogravimetric analysis of a polymorph of Form I.

Thermogravimetric analysis showed negligible weight loss of approximately 0.1% wt/wt or less from 25 to 250° C., as shown in FIG. 9.

At a ramp speed of 10° C./min using DSC Method A and a sample size of 5.31 mg, the DSC profile of a first batch of Form I displayed an endothermic peak at 60.1° C.

At a ramp speed of 10° C./min using DSC Method B and a sample size of 4.86 mg, the DSC profile of a second batch of Form I displayed an endothermic peak at 62.8° C.

Form II

Form II of COMPOUND I can be prepared according to the following methods.

Form II was prepared by dissolving COMPOUND I (2 g) in 1 mL of methanol. To this solution, 3 mL of distilled water was added, and precipitation was observed as soon as water was added. The solution was kept at room temperature overnight. The solid was filtered and dried under vacuum for about 4 hours. The solid was further dried in Genevac vacuum oven at 2 millibar at 40° C. for 60 hours to provide Form II (1.7 g).

Form II was also prepared by dissolving COMPOUND I (2 g) in 6 mL of acetone, and the solution was heated for 20 min. The acetone was removed as much as possible by evaporation. To this residue, 2 mL of reagent alcohol (90% ethanol, 5% methanol, and 5% isopropanol) was added followed by addition of 6 mL of water. Precipitation was observed as soon as water was added. The solution was kept in the freezer overnight. The solid COMPOUND I was filtered, washed with water and dried in Genevac vacuum oven at 2 millibar at 35° C. for 80 hours. A portion of the resulting solid COMPOUND I (200 mg) was heated until formation of liquid phase and further dried at 60° C. for 6 hours to provide Form II.

Form II was also prepared by dissolving COMPOUND I (30 g) in 30 mL of acetone, and the solution was heated for 20 min. The acetone was removed as much as possible by evaporation. To the residue, 30 mL of reagent alcohol was added followed by addition of 90 mL of water. Precipitation was observed as soon as water was added. The solution was kept at room temperature for 30 hours. The solid COMPOUND I was filtered, dried under vacuum for about 4 hours, and dried in Genevac vacuum oven at 2 millibar at 40° C. for 100 hours to provide Form II (26.0 g).

Form II was also prepared by dissolving COMPOUND I (2 g) in 1 mL of methanol, and the solution was cooled in an ice bath. To this solution, 3 mL of distilled water was slowly added while stirring. Stirring continued at room temperature for a few more hours. The solid COMPOUND I was filtered and dried in vacuum oven at 50° C. for 36 hours to provide Form II (1.7 g).

Form II was characterized by X-ray powder diffraction (XRPD), infrared spectroscopy, solid state $^{13}$C NMR, Raman spectroscopy, differential scanning calorimetry (DSC), and thermogravimetric analysis.

Crystalline Form II is characterized by the following X-ray powder diffraction pattern expressed in terms of the degree 2θ and relative intensities with a relative intensity of ≧6.0% measured on a Bruker D5000 diffractometer with CuKα radiation:

X-ray Powder Diffraction Peaks for Crystalline Form II

| Angle (Degree 2-θ) | Relative Intensity* % |
|---|---|
| 4.5 | 17.8 |
| 6.7 | 63.3 |
| 9.1 | 14.1 |
| 10.0 | 10.8 |
| 10.3 | 12.4 |
| 11.0 | 6.0 |
| 11.6 | 15.1 |
| 12.5 | 7.0 |
| 13.6 | 14.0 |
| 14.5 | 11.2 |
| 15.1 | 29.9 |
| 15.7 | 15.0 |
| 17.5 | 40.4 |
| 18.3 | 41.8 |
| 18.8 | 87.1 |
| 19.7 | 9.8 |
| 20.1 | 34.5 |
| 20.6 | 84.4 |
| 21.0 | 15.6 |
| 21.6 | 100.0 |
| 22.1 | 36.3 |
| 22.7 | 20.8 |
| 23.1 | 52.0 |
| 23.6 | 77.1 |
| 24.3 | 17.7 |
| 24.8 | 12.4 |
| 25.5 | 14.4 |
| 25.8 | 17.0 |
| 26.2 | 59.1 |
| 27.3 | 17.5 |
| 28.2 | 12.8 |
| 28.7 | 6.8 |
| 29.5 | 26.9 |
| 30.0 | 7.4 |
| 30.4 | 6.9 |
| 31.2 | 6.8 |
| 31.6 | 7.3 |
| 32.1 | 16.7 |
| 32.5 | 9.8 |
| 32.9 | 8.5 |
| 33.2 | 12.5 |
| 33.7 | 9.0 |
| 34.3 | 8.4 |
| 35.2 | 7.3 |
| 35.7 | 7.6 |
| 37.4 | 7.8 |
| 38.3 | 10.4 |
| 39.6 | 9.6 |

*The relative intensities may change depending on the crystal size and morphology.

Representative values of degree 2θ for Form II are 18.8 and 20.1.

Form II is characterized by the following $^{13}$C Solid State NMR chemical shifts:

$^{13}$C chemical shifts of Form II

| $^{13}$C Chemical Shifts$^a$ [ppm] | Intensity$^b$ |
|---|---|
| 158.6 | 5.0 |
| 153.6 | 12.0 |
| 149.0 | 6.1 |
| 140.1 | 5.7 |
| 133.0 | 6.1 |
| 132.3 | 3.6 |
| 128.9 | 5.4 |
| 127.6 | 5.4 |
| 126.8 | 6.5 |
| 125.6 | 8.0 |
| 123.2 | 4.1 |
| 121.6 | 5.3 |
| 119.9 | 5.1 |
| 114.4 | 8.4 |
| 110.5 | 3.9 |
| 67.4 | 3.5 |
| 51.8 | 1.7 |
| 29.6 | 5.4 |
| 28.6 | 6.7 |
| 23.8 | 4.1 |
| 15.5 | 6.1 |
| 9.4 | 1.7 |

$^a$Referenced to external sample of solid phase adamantane at 29.5 ppm.
$^b$Defined as peak heights. Intensities can vary depending on the actual setup of the CPMAS experimental parameters and the thermal history of the sample. CPMAS intensities are not necessarily quantitative.

Representative chemical shifts for Form II are as follows:

| Form II $^{13}$C Chemical Shifts [ppm] |
|---|
| 153.6 |
| 149.0 |
| 140.1 |
| 123.2 |
| 121.6 |
| 119.9 |
| 28.6 |

Form II is characterized by the following FT-IR peaks:

| FT-IR Peak Lists of Form II Wavelength (cm$^{-1}$) |
|---|
| 660 |
| 675 |
| 690 |
| 707 |
| 717 |
| 735 |
| 750 |
| 762 |
| 783 |
| 816 |
| 824 |
| 836 |
| 848 |
| 877 |
| 899 |
| 916 |
| 928 |
| 945 |
| 969 |
| 1004 |
| 1024 |
| 1046 |
| 1062 |

FT-IR Peak Lists of Form II
Wavelength (cm⁻¹)

-continued

| Wavelength (cm⁻¹) |
|---|
| 1075 |
| 1088 |
| 1105 |
| 1115 |
| 1135 |
| 1159 |
| 1178 |
| 1202 |
| 1239 |
| 1274 |
| 1290 |
| 1316 |
| 1325 |
| 1368 |
| 1395 |
| 1412 |
| 1425 |
| 1455 |
| 1462 |
| 1482 |
| 1502 |
| 1563 |
| 1576 |
| 1587 |
| 1617 |
| 1773 |
| 1898 |
| 1981 |
| 2022 |
| 2038 |
| 2052 |
| 2070 |
| 2164 |
| 2191 |
| 2259 |
| 2288 |
| 2324 |
| 2677 |
| 2725 |
| 2774 |
| 2783 |
| 2823 |
| 2865 |
| 2881 |
| 2898 |
| 2926 |
| 2950 |
| 2958 |
| 3030 |
| 3047 |
| 3061 |
| 3078 |
| 3090 |
| 3140 |

Representative FT-IR peaks for Form II are as follows:

| Form II Wavenumber (cm⁻¹) |
|---|
| 660 |
| 707 |
| 735 |
| 816 |
| 969 |
| 1024 |
| 1046 |
| 1135 |
| 1178 |

Form II is characterized by the following Raman peaks:

| Representative Raman Peaks of Form II |
|---|
| 137 |
| 156 |
| 193 |
| 257 |
| 277 |
| 300 |
| 326 |
| 374 |
| 395 |
| 419 |
| 435 |
| 443 |
| 465 |
| 474 |
| 483 |
| 506 |
| 520 |
| 536 |
| 567 |
| 590 |
| 621 |
| 634 |
| 646 |
| 660 |
| 676 |
| 693 |
| 708 |
| 722 |
| 750 |
| 772 |
| 795 |
| 825 |
| 837 |
| 852 |
| 878 |
| 900 |
| 915 |
| 947 |
| 1005 |
| 1027 |
| 1061 |
| 1089 |
| 1106 |
| 1134 |
| 1160 |
| 1180 |
| 1196 |
| 1223 |
| 1243 |
| 1277 |
| 1298 |
| 1324 |
| 1348 |
| 1370 |
| 1412 |
| 1441 |
| 1454 |
| 1467 |
| 1507 |
| 1563 |
| 1575 |
| 1589 |
| 1617 |
| 2728 |
| 2783 |
| 2825 |
| 2868 |
| 2879 |
| 2917 |
| 2931 |
| 2957 |
| 3014 |

-continued

| Representative Raman Peaks of Form II |
| --- |
| 3031 |
| 3066 |
| 3137 |
| 3174 |
| 3226 |

Particularly representative Raman peaks for Form II are as follows:

| Form II Wavenumber (cm$^{-1}$) |
| --- |
| 257 |
| 300 |
| 326 |
| 590 |
| 646 |
| 1180 |
| 1348 |
| 1370 |

Figure 10:
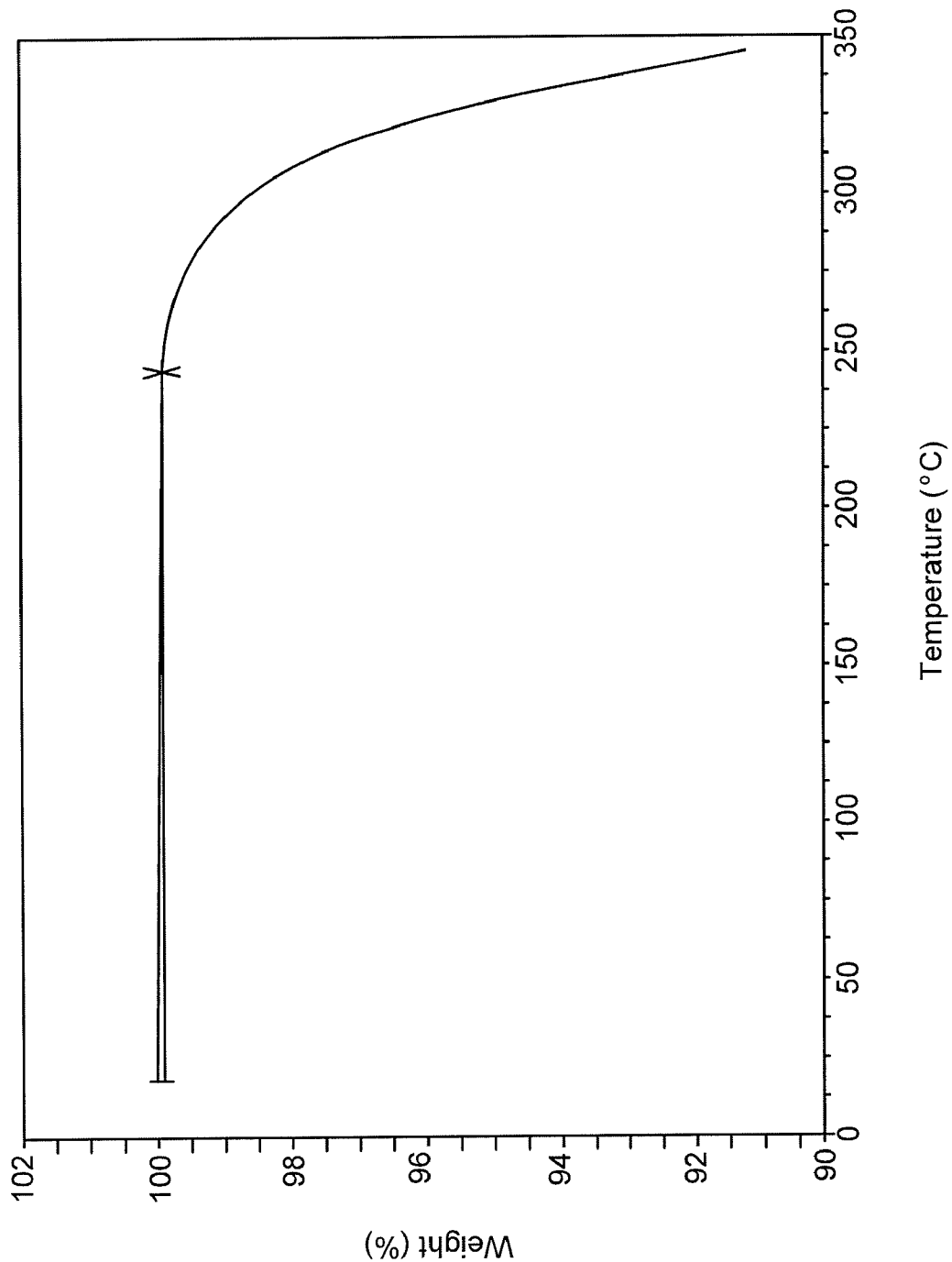
FIG. 10 is a thermogravimetric analysis of a polymorph of Form II.

Thermogravimetric analysis showed negligible weight loss of approximately 0.1% wt/wt or less from 25 to 250° C., as shown in FIG. 10.

At a ramp speed of 10° C./min using DSC Method A and a sample size of 4.87 mg, the DSC profile of a first batch of Form II displayed an endothermic peak at 58.9° C.

At a ramp speed of 10° C./min using DSC Method B and a sample size of 6.38 mg, the DSC profile of a second batch of Form II displayed an endothermic peak at 62.5° C.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the present invention.

The invention claimed is:

1. A polymorph of [3-(4-{2-butyl-1-[4-(4-chloro-phenoxy)-phenyl]-1H-imidazol-4-yl}-phenoxy)-propyl]-diethylamine, having a solid state $^{13}$C NMR spectrum comprising peaks at 153.6, 140.1 and 119.9 ppm, when the upfield resonance of crystalline adamantane is set to 29.5 ppm.

2. The polymorph of claim 1, having a solid state $^{13}$C NMR spectrum comprising peaks at 153.6, 149.0, 140.1, 119.9, and 28.6 ppm, when the upfield resonance of crystalline adamantane is set to 29.5 ppm.

3. The polymorph of claim 2, having a solid state $^{13}$C NMR spectrum comprising peaks at 153.6, 149.0, 140.1, 123.2, 121.6, 119.9, and 28.6 ppm, when the upfield resonance of crystalline adamantane is set to 29.5 ppm.

4. The polymorph of claim 1, having IR absorption maxima at 816, 1046 and 1178 cm$^{-1}$.

5. The polymorph of claim 4, having IR absorption maxima at 660, 707, 735, 816, 969, 1024, 1046, 1135 and 1178 cm$^{-1}$.

6. The polymorph of claim 1, having a Raman spectrum comprising Raman shifts of 300 and 1180 cm$^{-1}$.

7. The polymorph of claim 6, having a Raman spectrum comprising Raman shifts of 257, 300, 326, 590, 646, 1180, 1348 and 1370 cm$^{-1}$.

8. A polymorph of [3-(4-{2-butyl-1-[4-(4-chloro-phenoxy)-phenyl]-1H-imidazol-4-yl}-phenoxy)-propyl]-diethylamine, having an X-ray powder diffraction comprising the following 2θ values, measured using CuKα radiation having a wavelength of 1.54056 Å: 18.8 and 20.1 degrees.

9. The polymorph of claim 8, having IR absorption maxima at 816, 1046 and 1178 cm$^{-1}$.

10. The polymorph of claim 9, having IR absorption maxima at 660, 707, 735, 816, 969, 1024, 1046, 1135 and 1178 cm$^{-1}$.

11. The polymorph of claim 8, having a Raman spectrum comprising Raman shifts of 300 and 1180 cm$^{-1}$.

12. The polymorph of claim 11, having a Raman spectrum comprising Raman shifts of 257, 300, 326, 590, 646, 1180, 1348 and 1370 cm$^{-1}$.

13. A polymorph of [3-(4-{2-butyl-1[4-(4-chloro-phenoxy)-phenyl]-1H-imidazol-4-yl}-phenoxy)-propyl]-diethylamine, having a Raman spectrum comprising Raman shifts of 300 and 1180 cm$^{-1}$.

14. The polymorph of claim 13, having a Raman spectrum comprising Raman shifts of 257, 300, 326, 590, 646, 1180, 1348 and 1370 cm$^{-1}$.

15. The polymorph of claim 1, 8, or 13, where the polymorph exists in a form that is substantially free of Form I of [3-(4-{2-butyl-1[4-(4-chloro-phenoxy)-phenyl]-1H-imidazol-4-yl}-phenoxy)-propyl]-diethylamine.

16. A method of producing a polymorph of [3-(4-{2-butyl-1-[4-(4-chloro-phenoxy)-phenyl]-1H-imidazol-4-yl}-phenoxy)-propyl]-diethylamine comprising:

(a) dissolving [3-(4-{2-butyl-1[44-(4-chloro-phenoxy)-phenyl]-1H-imidazol-4-yl}-phenoxy)-propyl]-diethylamine in a solvent system comprising an alcoholic solvent;

(b) adding a precipitating solvent to the solvent system such that [3-(4-{2-butyl-1[4-(4-chloro-phenoxy)-phenyl]-1H-imidazol-4-yl}-phenoxy)-propyl]-diethylamine precipitates from the solvent system; and (c) recovering the precipitate from the solvent system.

17. The method of claim 16, wherein the alcoholic solvent is selected from the group consisting of methanol, ethanol, isopropanol, and mixtures thereof.

18. The method of claim 16, wherein the precipitating solvent is water.

19. The method of claim 16, wherein the polymorph of [3-(4-{2-butyl-[1-[4-(4-chloro-phenoxy)-phenyl]-1H-imidazol-4-yl}-phenoxy)-propyl]-diethylamine comprises Form II.

* * * * *